United States Patent [19]

Borcherding et al.

[11] Patent Number: 5,001,236

[45] Date of Patent: Mar. 19, 1991

[54] BENZOTHIAZEPINES

[75] Inventors: David R. Borcherding, Roeland Park, Kans.; Daniel E. Martin, Lee's Summit, Mo.

[73] Assignee: Marion Laboratories, Inc., Kansas City, Mo.

[21] Appl. No.: 440,383

[22] Filed: Nov. 22, 1989

[51] Int. Cl.$^5$ .................... C07D 513/04; A61K 31/55
[52] U.S. Cl. .................................................. 340/491
[58] Field of Search ........................................ 540/491

[56] References Cited

U.S. PATENT DOCUMENTS

| | | | |
|---|---|---|---|
| 3,075,967 | 1/1963 | Krapcho | 540/491 |
| 3,562,257 | 2/1971 | Kugita et al. | 540/491 |
| 4,512,988 | 4/1985 | Weller et al. | 540/491 X |
| 4,567,175 | 1/1986 | Takeda et al. | 540/491 X |
| 4,584,131 | 4/1986 | Floyd et al. | 540/491 |

*Primary Examiner*—Robert T. Bond

[57] ABSTRACT

Certain 1,5-benzothiazepines are useful intermediates or pharamceuticals.

18 Claims, No Drawings

BENZOTHIAZEPINES

FIELD

This invention concerns benzothiazepines, useful as intermediates or pharmaceuticals.

BACKGROUND

Various useful benzothiazepines are known. See, patents classified in U.S. Pat. class 540 subclass 491, e.g., the following, incorporated herein by reference: Krapcho, U.S. Pat. No. 3,075,967 (Jan. 29, 1963); Kugita et al., U.S. Pat. No. 3,562,257 (Feb. 9, 1971); Weller, III et al., U.S. Pat. No. 4,512,988 (Apr. 23, 1985); Takeda et al., U.S. Pat. No. 4,567,175 (Jan. 28, 1986); Floyd et al., U.S. Pat. No. 4,584,131 (Apr. 22, 1986). Such art discloses that these compounds are useful, as may be appropriate, as drugs for the treatment of Parkinsonsim, as antidepressants, as tranquilizers, as coronary vasodilators, as hypotensive agents, as cerebral vasodilators, as antiarrhythmic agents, as anti-anginal agents, as antifibrillatory agents as anti-asthmatic agents, and in limiting myocardial infarction.

The art lacks and needs further benzothiazepines, to include those having other uses.

SUMMARY

Provided is a Compound/Salt, i.e., a compound, or salt thereof, or compound salt, selected from among those represented by the following general formula:

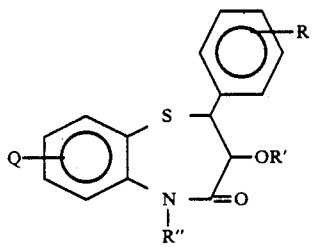

(I)

wherein:

Q is hydro (H) or halo to include fluoro (F) and chloro (Cl), especially H or 8-Cl;

R is lower alkoxy (OLA) or lower haloalkyl (LHA), to include para-methoxy (pOMe) or para-trifluoromethyl (pCF3);

R' is H or alkylacyl to include, e.g., adamantylcarbox and lower alkylacyl, especially H or lower alkylacyl to include groups such as acetyl, propionyl, butyryl, valeryl, isovaleryl, pivalyl, etc., and R" is 2-(dimethylamino)ethyl (R"1a), 2-(piperidino)ethyl (R"5) or (N-pyridinium)alkyl with a suitable counterion being present (+R"9-X) to include 2-(N-pyridinium)ethyl with a bromide and/or chloride counterion being present (+R'9a-X), with cis-or trans- referring to configurations about positions 2 & 3 of the benzothiazepine nucleus, the absence of either of these in nomenclature meaning that either or both of these configurations can be present and with generally either or both optical antipodes able to be present, and further being identified as follows:

| Compound/Salt | Q | R | R' | R" |
|---|---|---|---|---|
| ML106Q' | H | OLA or LHA | H or alkylacyl | +R"9-X |
| ML106Q" | halo | OLA or LHA | H or alkylacyl | +R"9-X |
| ML1065 | H | pOMe | H | +R"9a-X |
| ML1066 | H | pOMe | acetyl | +R"9a-X |
| cis-ML1065 | H | pOMe | H | +R"9a-X |
| cis-ML1066 | H | pOMe | acetyl | +R"9a-X |
| trans-ML1078 | H | pCF3 | H | R"1a |
| cis-ML1080 | H | pOMe | adamantylcarboxy | R"1a |
| trans ML1082 | H | pCF3 | H | R"5 |
| trans-ML1096 | 8-Cl | pOMe | H | R"5 |
| trans-ML1103 | H | pOMe | H | R"5. |

These are useful intermediates or pharmaceuticals, which can possess activity as antidepressants, tranquilizers and/or coronary vasodilators. Furthermore, certain of these surprisingly are effective, even excellent, anti-cancer drug potentiators, e.g., trans-ML1065, cis-ML1066, cis-ML1078, trans-ML1082, trans-ML1096 and especially trans-ML1103, and/or excellent ameliorators for generalized tonic-clonic epileptic type seizures in mammals, e.g., trans-ML1078, trans-ML1082 and trans-ML1096.

Further advantages attend this invention as well.

ILLUSTRATIVE DETAIL

The compounds and compound salts of this invention can be made by reacting a suitable glycidic acid ester with a suitable aminothiophenol to prepare corresponding aminophenylthiopropionic acid ester, then cyclyzing the latter ester or its corresponding free acid, followed by N-alkylation and 3-acylation as may be desired. Suitable glycidic acid esters may be found in the prior art, or they can be prepared by other methods. See e.g., Wynberg et al., U.S. Pat. Appl. Ser. No. 07/195,749 filed 05/18/88, now U.S. Pat. No. 4,885,575 (Dec. 5, 1989); Wynberg et al., U.S. Pat. Appl. Ser. No. 07/439,678 entitled, "GLYCIDIC ACID ESTERS BY BAEYER-VILLAGER REARRANGEMENTS," and filed on even date herewith, both incorporated herein by reference. See also, Martin, U.S. Pat. Appl. Ser. No. 07/195,709 filed 05/18/88, incorporated herein by reference. Compound/Salts can be prepared by N-alkylation of known 5-hydro-1,5-benzothiazepin-4(5H)-ones. See e.g., Kugita et al., supra, and Takeda et al., supra.

On the one hand, the benzothiazepine compounds of this invention may be present as a free or neutral amino compound. Alternatively, they may be present as a salt thereof, typically where an alkyl amino nitrogen is cationic and a suitable anion accompanies this salt.

Salts of the benzothiazepine compounds of this invention include suitable pharmaceutically acceptable salts. Suitable pharmaceutically acceptable salts generally include such salts as the hydrochloride, the fumerate, the sulfate, the citrate, the maleate, and so forth.

On the other hand, benzothiazepine compound salts of this invention have the R" moiety as represented in the formula I being the (N-pyridinium)alkyl with a suitable counterion (+R"9-X) group. The +R"9-X group can be represented by a group of the following general formula:

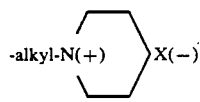
(Ia)

wherein the alkyl moiety is bonded to the nitrogen at the 5-position of the benzothiazepine nucleus of the compound of the formula I and is bonded through the cationic pyridinium nitrogen, which alkyl moiety can be, e.g., ethylenyl and the X(−) represents a suitable counterion (anion), which is advantageously bromide and/or chloride, which can simply be left with the compound salt from its preparation.

Any person skilled in the art can use the compounds or salts of this invention with the summary above. See also, Ahmed, U.S. Pat. Appl. Ser. No. 07/441,083 entitled, "CANCER DRUG POTENTIATORS," and filed on even date herewith; Zobrist et al., U.S. Pat. Appl. Ser. No. 07/440,376 entitled, "BENZO-THIAZEPINE ANTI-SEIZURE METHOD," and filed on even date herewith, both incorporated herein by reference.

The following examples further illustrate this invention. In the examples, parts, percentages and ratios are by weight.

EXAMPLE 1

Preparation of dl-cis-ML1065

Under a nitrogen blanket, 7.47 g of 80 percent sodium hydride (Aldrich; 0.249 mol) and 600 mL of anhydrous dimethyl sulfoxide (DMSO) were added to a 2-L round bottom flask, which had been fitted with a reflux condenser, nitrogen adapter and magnetic stirrer. The resulting solution was stirred for 45 minutes, and then 50.0 g of dl-cis-2-(4-methoxyphenyl)-2,3-dihydro-3-hydroxy-1,5-benzothiazepin-4(5H)-one (0.166 mol) was added in two portions over a ten minute period. A fairly vigorous evolution of hydrogen gas ensued. The reaction mixture was stirred for 50 minutes, and then 40 mL of anhydrous 1,2-dichloroethane (Aldrich; 0.508 mol) was added all at once. The reaction mixture was stirred for 40 hours, whereupon 750 mL of cold water was added thereto. Ether was used to extract the desired alkylated product, which was dried over drying agent. This product was taken up with dichloromethane, and it was dried further. The product was chromatographed on 70-230 mesh silica gel column, with a 2:1 hexane to ethyl acetate eluent. Concentration under high vacuum yielded 15.05 g of dl-cis-2-(4-methoxyphenyl)-2,3-dihydro-3-hydroxy-5-(2-chloroethyl)-1,5-benzothiazepin-4(5H)-one (24.9 percent of theory).

The 15.05 g of dl-cis-2-(4-methoxyphenyl)-2,3-dihydro-3-hydroxy-5-(2-chloroethyl)-1,5-benzothiazepin-4(5H)-one (0.0414 mol) was dissolved in 350 mL of anhydrous pyridine (Aldrich; 4.14 mol), and this mixture was placed into a 500-mL round bottom flask, which had been fitted with a reflux condenser, nitrogen adapter and magnetic stirrer, all glassware having been oven-dried. Under a nitrogen blanket, 4.416 g of lithium bromide (Aldrich; 0.0508 mol) was added to the flask contents. The resulting mixture was stirred and heated at about 73 degrees C. for about 17 hours. whereupon the heat was raised slightly with continued stirring for another 5 hours and 20 minutes. The reaction mixture was then allowed to cool to room temperature, and it was mixed with ether, forming an oil, and the ether layer was decanted. The oil was dissolved in a mixture of 156 mL of n-heptane and 62 mL of methanol. This was concentrated under high vacuum at 44 degrees C. An oily solid resulted, to which 100 mL of warm methanol was added. Solid was filtered therefrom, leaving a mother liquor. The solid was rinsed with ether, then acetone, and then a slight amount of methanol, and it was dried to yield a first crop of 9.07 g. To the mother liquor was added 175 mL of ether, and the mixture was stirred for a short time at room temperature. Another 200 mL of ether was added, with stirring. A second crop of solid resulted and was filtered, rinsed well with ether, then acetone, then a slight amount of methanol, and it was dried to yield 1.96 g. Total yield of product dl-cis-2-(4-methoxyphenyl)-2,3-dihydro-3-hydroxy-5-[2-(N-pyridinium)ethyl]-1,5-benzothiazepin-4(5H)-one bromide/chloride (salt) was 11.03 g (about 55 percent of theory). Further drying of both solid product samples under high vacuum was carried out. The solid product was present as a 1:1 molar solvate with the methanol. High pressure liquid chromatography (HPLC) indicated 98.3 percent purity of the product. Elemental analysis of the first crop, found: C, 55.91; 55.85. H, 5.24; 5.17. N, 5.46; 5.43. Cl, 1.19; 1.25. S, 6.23; 6.15. Br, 7.41; 7.34.

EXAMPLE 2

Preparation of dl-cis-ML1066

Under a nitrogen blanket, to 4.50 g (0.00924 mol) of the dl-cis-ML1065 from Example 1, in a 25-mL round bottom flask, which had been fitted with a reflux condenser, nitrogen adapter and magnetic stirrer, was added a mixture composed of 4.5 mL of acetic anhydride and 4.5 mL of glacial acetic acid. The resulting mixture was stirred for 17 hours in the flask in an oil bath at about 105 degrees C. The flask and its contents were removed from the oil bath. The mixture was diluted with methanol, and the methanolic mixture was concentrated under high vacuum to remove acetic acid and acetic anhydride, leaving an oil. The oil was with hexane, and a hexane azeotrope was used to remove traces of acetic acid. The product in oil form was crystallized by dissolving it in about 15 mL of methanol and adding about 33 mL of ether. An additional 70 mL of ether was added to obtain further crystallization. This yielded a first crop of 4.31 g of solid dl-cis-2-(4-methoxyphenyl)-2,3-dihydro-3-acetyloxy-5-{[2-(N-pyridinium)ethyl]}-1,5-benzothiazepin-4(5H)-one bromide/chloride (ester salt) (88.1 percent yield of theory). HPLC indicated 100 percent purity. Elemental analysis of the first crop: Found: C, 55.95; 55.89. H, 4.88; 4.90. N, 5.20; 5.11. Cl, 0.97; 0.86. S, 6.01; 5.88. Br, 7.17; 6.92.

EXAMPLE 3

A. Preparation of dl-trans-ML1078 & 1082 intermediates

To 150 mL of dry methanol was added 3.93 g of sodium (0.121 mol). Slowly with stirring, to the freshly made sodium methoxide solution was added 24.72 g of 4-trifluoromethylbenzaldehyde (0.142 mol) and a solution of 18.55 g of methyl chloroacetate (0.171 mol) in 75 mL of dry methanol. After stirring for 2 hours at 0 degrees C., the resulting reaction mixture was poured onto ice and extracted with ethyl acetate. The ethyl acetate layer was dried and concentrated to give 24.6 g of a product of dl-trans-(4-trifluoromethylphenyl)glycidic acid, methyl ester.

All of the dl-trans-(4-trifluoromethylphenyl)glycidic acid, methyl ester (0.1 mol) and 12.5 g of 2-aminothiophenol (0.1 mol) were refluxed in 120 mL of toluene overnight. Cooling of the resulting reaction mixture in a freezer for 3 hours provided a precipitate, which was filtered, washed with an ice-cold 1:1 solution of hexane to ethyl acetate, and dried under vacuum to give 15.0 g of a product of dl-threo-2-hydroxy-3-(2-aminophenylthio)-3-(4-trifluoromethylphenyl)propionic acid, methyl ester.

All of the dl-threo-2-hydroxy-3-(2-aminophenylthio)-3-(4-trifluromethylphenyl) propionic acid, methyl ester (0.0416 mol) was saponified with 3.0 g of potassium hydroxide (0.054 mol) by boiling a mixture of these in 100 mL of water for 45 minutes. The resulting mixture was then cooled with an ice bath, and the pH was adjusted to from 3.5 to 4.0 with 6 N aqueous hydrochloric acid. A white precipitate was collected by filtration and washed with 100 mL of water. The solid was placed in a 500-mL flask and refluxed in 150 mL of xylene for 6 hours, with water removed with a Dean-Stark trap. Cooling, to include in an ice bath, resulted in precipitation. The precipitate was collected by filtration and dried under vacuum to give 9.6 g. of dl-trans-2-(4-trifluoromethylphenyl)-2,3-dihydro-3-hydroxy-1,5-benzothiazepin-4(5H)-one.

B. Preparation of dl-trans-ML1078

A 2.0 g sample of the dl-trans-2,3-dihydro-2-(4-trifluoromethylphenyl) -3hydroxy-1,5-benzothiazepin-4(5H)-one from part A above 5.9 mmol) was dissolved in 70 mL of ethyl acetate; 1.35 g of 1-chloro -2-(N-dimethylamino)ethane hydrochloride (9.4 mmol), 1.65 g of potassium carbonate (12.0 mmol) and 3 mL of water were added, and the resulting mixture was refluxed overnight. The resulting reaction mixture was cooled, extracted with water and then brine, and the organic layer was dried over anhydrous sodium sulfate and concentrated. The concentrated material was taken up with diethyl ether, and anhydrous hydrogen chloride gas was passed therethrough. A white precipitate formed, which was filtered, collected and dried under vacuum to yield 2.0 g of dl-cis-2-(4-trifluoromethylphenyl)-2,3-dihydro-3-hydroxy -5-[2-(N-dimethylamino)ethyl]-1,5-benzothiazepin-4(5H)-one hydrochloride (salt).

C. Preparation of dl-trans-ML1082

A 1.0 g sample of the dl-trans-2,3-dihydro -2-(4-trifluoromethylphenyl)-3-hydroxy-1,5-benzothiazepin -4(5H)-one from part A above (3.0 mmol) was dissolved in 50 mL of ethyl acetate; 0.88 g of 1-(2-chloroethyl)-piperidine monohydrochloride (4.8 mmol), 1.2 g of potassium carbonate (9.0 mmol) and 4 mL of water were added, and the resulting mixture was refluxed overnight. The resulting reaction mixture was cooled, extracted with water and then brine, and the organic layer was dried over anhydrous sodium sulfate and concentrated. This concentrated material was dissolved in a solvent of 9:1 dichloromethane to ethanol and applied to a column containing 25 g of 230:400 mesh silica gel, which was eluted with a solvent of 9:1 dichloromethane to ethanol. The eluent was concentrated; the concentrated eluent was taken up with toluene, and anhydrous hydrogen chloride gas was passed thrrethrough. A white precipitate formed, which was filtered, collected and dried under vacuum to yield 1.13 g of dl-trans-2-(4-trifluoromethylphenyl)-2,3-dihydro-3-hydroxy -5-[2-(N-piperidino)ethyl]-1,5-benzothiazepin-4(5H)-one hydrochloride (salt).

EXAMPLE 4

Preparation of dl-cis-ML1080

A mixture of 5.0 g of dl-cis-2-(4-methoxyphenyl) -2,3-dihydro-3-hydroxy-5-[2-(N-dimethylamino)ethyl]-1,5-benzothiazepin-4(5H)-one (13.4 mmol) and 3.45 g of adamantylcarboxylic acid chloride (17.4 mmol) in 30 mL of pyridine was cooled to 0 degrees C. and placed in a refrigerator overnight. The resulting reaction mixture was concentrated, taken up in dichloromethane and extracted thus with water and then brine, then dried over anhydrous sodium sulfate, and concentrated to an oil. The oil was dissolved in dichloromethane and applied to silica gel, which was eluted with a solvent of 9:1 dichloromethane to ethanol. The eluent was concentrated and taken up with ethyl acetate. A sample of 1.5 g of fumaric acid (13.4 mmol) was added, and the resulting mixture was heated to dissolution, adding 1.0 mL of ethanol. The solution was concentrated and vacuum dried for 36 hours to yield dl-cis-2-(4-methoxyphenyl) -2,3-dihydro-3-adamantylcarboxy-5-[2-(N-dimethylamino)ethyl]-1,5-benzothiazepin-4(5H)-one fumarate (salt).

EXAMPLE 5

Preparation of dl-trans-ML1096

To a 100-mL round bottom flask was added 1.98 g of dl-trans-2-(4-methoxyphenyl)-2,3-dihydro-3-hydroxy -8-chloro-1,5-benzothiazepin-4(5H)-one (5.9 mmol), then 16 mL of ethyl acetate and 1.0 mL of water, next 1.19 g of 1-(2-chloroethyl)piperidine monohydrochloride (6.5 mmol) and 1.80 g of anhydrous potassium carbonate (13.0 mmol). The resulting mixture was stirred at about 77 degrees C. for 17¼hours, cooled to room temperature, washed well three times with water, and the organic layer was concentrated to obtain about 3 g of a beige colored solid. The solid was taken up with 2-butanone; anhydrous hydrogen chloride gas was passed therethrough, and solvent was removed, giving an oily solid. Mixing with ether gave 2.62 g of salt product, which was dried. A 0.531 g sample of the salt product was dissolved in a heated mixture of about 7 mL of reagent ethanol and 4 mL of trichloromethane. The addition of 23 mL of ether and cooling in ice gave solid product, which was filtered, rinsed well with ether and dried to yield a first crop of 0.373 g. The remaining salt product, about 2.089 g, was dissolved in a heated mixture of 28 mL of reagent and 16 mL of trichloromethane. The addition of 90 mL of ether, stirring at room temperature and cooling in ice gave solid product, which was filtered, rinsed with ether and dried to yield a second crop of 1.492 g. The total yield of dl-trans-2-(4-methoxyphenyl) -2,3-dihydro-3-hydroxy-5-[2-(N-piperidino)ethyl]-8-chloro -1,5-benzothiazepin-4(5H)-one hydrochloride (salt) was 1.865 g (65.2 percent of theory). HPLC analysis indicated 98.4 percent purity. Elemental analysis of the first crop, Calculated: C, 57.14; H, 5.84; 0, 9.93; N, 5.79; S, 6.63; Cl, 14.67. Found: C, 56.84; 56.82. H, 5.74; 5.75. N, 5.65; 5.63. S, 6.15; 6.27. Cl, 15.08; 15.13.

EXAMPLE 6

Preparation of dl-trans-ML1103

Refluxed overnight was a mixture of 2.0 g of dl-trans-2-(4-methoxyphenyl)-2,3-dihydro-3-hydroxy -1,5-benzothiazepin-4(5H)-one (6.64 mmol), 5.4 g of 1-(2-chloroethyl)piperidine monohydrochloride (29 mmol), 7.1 g of anhydrous potassium carbonate (51 mmol), 74.8 mL of ethyl acetate, and 6.6 mL of water. The resulting mixture was cooled, washed with water and then brine, dried over anhydrous sodium sulfate, and concentrated under vacuum. A silica gel column chromatographic purification using an eluent of a 9:1 ethyl acetate to ethanol solution was performed, and solvent was removed from cuts containing product under vacuum. Product was dissolved in 200 mL of and anhydrous hydrogen chloride gas was passed therethrough. The resulting mixture was concentrated, and salt product was recrystallized from ethanol, filtered, rinsed with ether and dried under vacuum to yield dl-trans-2-(4-methoxyphenyl)-2,3-dihydro-3-hydroxy -5-[2-(N-piperidino)ethyl]-1,5-benzothiazepin-4(5H)-one hydrochloride (salt).

CONCLUSION

The present invention is thus provided. Numerous adaptations and modifications can be effected by those skilled in the art within the spirit of this invention, the scope of which is particularly pointed out by the following distinctly claimed subject matter.

What is claimed is:

1. A compound of the formula:

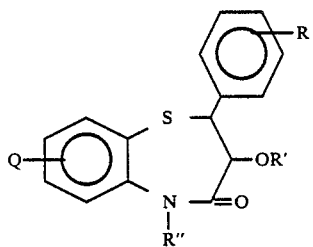

(I)

or its pharmaceutically acceptable salts or compound salts, wherein:

Q is hydro or halo;
R is lower alkoxy or lower haloalkyl;
R' is hydro or alkylacyl; and
R" is (N-pyridinium) alkyl with a suitable counterion being present,
said compound having a cis or trans configuration about positions 2 and 3 of the benzothiazepine nucleus, and with generally either or both optical antipodes able to be present.

2. The compound in accordance with claim 1, wherein R" is 2-(N-pyridinium)ethyl with a bromide and/or chloride counterion being present.

3. The compound in accordance with claim 2, wherein Q is hydro, R is para-methoxy, and R' is hydro or acetyl.

4. The compound in accordance with claim 3, which is cis-2-(4-methoxyphenyl)-2,3-dihydro-3hydroxy-5[2-(N-pyridinium)ethyl] -1,5-benzothiazepin-4(5H)-one bromide/chloride or cis-2-(4-methoxyphenyl) -2,3-dihydro-3-acetyloxy-5[2-(N-pyridinium)ethyl]-1,5-benzothiazepin-4(5H)-one bromide/chloride.

5. A compound in accordance with claim 4, which is cis-2-(4-methoxyphenyl) -2,3-dihydro-3-hydroxy-5[2-(N-pyridinium)ethyl]-1,5-benzothiazepin-4(5H)-one bromide/chloride.

6. The compound in accordance with claim 5, with bromide and chloride counterions being present.

7. The compound in accordance with claim 4, which is cis-2-(4-methoxyphenyl)-2,3-dihydro-3-acetyloxy-5-[2-(N-pyridinium) -ethyl]-1,5-benzothiazepin-4(5H)-one bromide/chloride.

8. The compound in accordance with claim 7, with bromide and chloride counterions being present.

9. A compound of the formula:

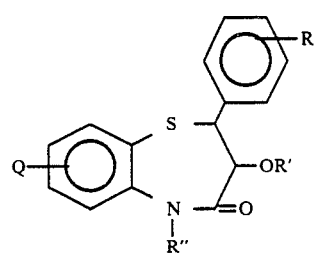

(I)

or its pharmaceutically acceptable salts, wherein:

Q is hydro;
R is para-trifluoromethyl;
R' is hydro; and
R" is 2-(dimethylamino)ethyl,
said compound having a trans configuration about positions 2 and 3 of the benzothiazepine nucleus, and with generally either or both optical antipodes able to be present.

10. The compound in accordance with claim 9, which is a hydrochloride salt.

11. A compound of the formula:

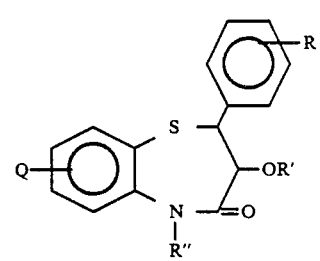

(I)

or its pharmaceutically acceptable salts, wherein:

Q is hydro;
R is para-methoxy;
R' is adamantylcarboxy; and
R" is 2-(dimethylamino)ethyl,
said compound having a cis configuration about positions 2 and 3 of the benzothiazepine nucleus, and with generally either or both optical antipodes able to be present.

12. The compound in accordance with claim 11, which is a fumarate salt.

13. A compound of the formula:

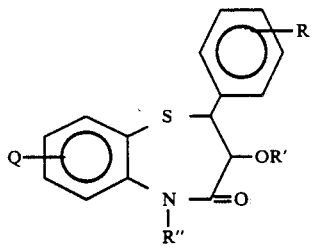

or its pharmaceutically acceptable salts, wherein:

Q is hydro;

R is para-trifluoromethyl;

R' is hydro; and

R" is 2-(piperidino)ethyl, said compound having a trans configuration about positions 2 and 3 of the benzothiazepine nucleus, and with generally either or both optical antipodes able to be present.

14. The compound in accordance with claim 13, which is a hydrochloride salt.

15. A compound of the formula:

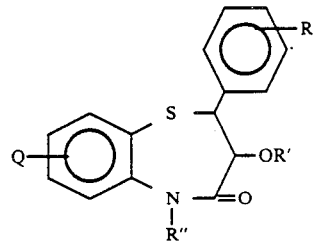

or its pharmaceutically acceptable salts, wherein:
Q is 8-chloro;
R is para-methoxy;
R' is hydro; and
R" is 2-(piperidino)ethyl,
said compound having a trans configuration about positions 2 and 3 of the benzothiazepine nucleus, and with generally either or both optical antipodes able to be present.

16. The compound in accordance with claim 15, which is a hydrochloride salt.

17. A compound of the formula:

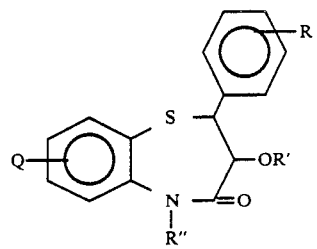

or its pharmaceutically acceptable salts, wherein:
Q is hydro;
R is para-methoxy;
R' is hydro; and
R" is 2-(piperidino)ethyl,
said compound having a trans configuration about positions 2 and 3 of the benzothiazepine nucleus, and with generally either or both optical antipodes able to be present.

18. The compound in accordance with claim 17, which is a hydrochloride salt.

* * * * *

UNITED STATES PATENT AND TRADEMARK OFFICE
CERTIFICATE OF CORRECTION

PATENT NO. : 5,001,236

DATED : March 19, 1991

INVENTOR(S) : David R. Borcherding and Daniel E. Martin

It is certified that error appears in the above-identified patent and that said Letters Patent is hereby corrected as shown below:

At column 1, line 62, the patent reads "adamantylcarbox" and should read --adamantylcarboxy--. At column 2, line 2, the patent reads "(+R'9a-X)" and should read -- (+R"9a-X) --. At column 2, line 27, the patent reads "trans-ML1065" and should read --cis-ML1065--. At column 2, line 28, the patent reads "cis-ML1078" and should read --trans-ML1078--. Column 2, line 45, the patent reads "No. 4,885,575" and should read --No. 4,885,375--. At column 4, line 45, the patent reads "oil was with" and should read --oil was mixed with--. At column 5, line 15, the patent reads "Allof" and should read --All of--. At column 5, line 32, the patent reads "-3hydroxy" and should read -- -3-hydroxy --. At column 5, line 46, the patent reads "dl-cis" and should read --dl-trans--. At column 5, line 67, the patent reads "thrrethrough" and should read --therethrough--. At column 6, line 53, the patent reads "of reagent and 16 ml" and should read --of reagent ethanol and 16 ml--

UNITED STATES PATENT AND TRADEMARK OFFICE
CERTIFICATE OF CORRECTION

PATENT NO. : 5,001,236

DATED : March 19, 1991

INVENTOR(S) : David R. Borcherding et al

It is certified that error appears in the above-identified patent and that said Letters Patent is hereby corrected as shown below:

column 7, line 13, the patent reads "200 mL of and" and should read --200 mL of toluene, and-- column 7, line 61, claim 4, the patent reads "3hydroxy" and should read --3-hydroxy--. At column 7, line 68, claim 5, the patent reads "-5[2-" and should read -- -5-[2- --.

Signed and Sealed this

Nineteenth Day of January, 1993

*Attest:*

DOUGLAS B. COMER

*Attesting Officer*     *Acting Commissioner of Patents and Trademarks*